United States Patent [19]

Cochrum

[11] Patent Number: 5,470,731
[45] Date of Patent: Nov. 28, 1995

[54] COATED TRANSPLANT AND METHOD FOR MAKING SAME

[75] Inventor: Kent C. Cochrum, Davis, Calif.

[73] Assignee: The Regents of the University of California, Oakland, Calif.

[21] Appl. No.: 255,577

[22] Filed: Jun. 8, 1994

Related U.S. Application Data

[63] Continuation of Ser. No. 890,896, May 19, 1992, abandoned.

[51] Int. Cl.$^6$ .............................. A61K 9/107; A61F 2/02; A01N 1/02; C12N 11/04
[52] U.S. Cl. .............................. 435/182; 435/1; 435/177; 435/240.22; 435/240.243; 424/424; 427/2.1
[58] Field of Search .................... 424/423, 424; 435/1, 177, 182, 240, 241, 240.22, 240.243; 264/4; 427/2.1

[56] References Cited

U.S. PATENT DOCUMENTS

| | | | |
|---|---|---|---|
| 4,352,883 | 10/1982 | Lim | 435/178 |
| 4,391,909 | 7/1983 | Lim | 435/178 |
| 4,407,957 | 10/1983 | Lim | 435/178 |
| 4,409,331 | 10/1983 | Lim | 435/178 |
| 4,647,536 | 3/1987 | Mosbach et al. | 435/177 |
| 4,663,286 | 5/1987 | Tsang et al. | 435/178 |
| 4,673,566 | 6/1987 | Goosen et al. | 435/178 |
| 4,689,293 | 8/1987 | Goosen et al. | 435/1 |
| 4,696,286 | 9/1987 | Cochrum | 435/182 |
| 4,744,933 | 5/1988 | Rha et al. | 264/4.3 |
| 4,749,620 | 6/1988 | Rha et al. | 428/402.2 |
| 4,778,749 | 10/1988 | Vasington et al. | 435/178 |
| 4,803,168 | 2/1989 | Jarvis, Jr. | 435/177 |
| 4,806,355 | 2/1989 | Goosen et al. | 424/424 |

FOREIGN PATENT DOCUMENTS 2034641  5/1992  Canada .

OTHER PUBLICATIONS

Nilsson, K., et al., "Entrapment of Animal Cells for Production of Monoclonal Antibodies and Other Biomolecules", Nature, 302:629–630 (1983).
Transplantation Proceedings, 14 4:714–723 (1982).
Diabetes, 26:1136–9 (1977).
Trans.Am.Soc.Artif.Intern. Organs 25:74–76 (1979).

*Primary Examiner*—Carlos A. Azpuru
*Attorney, Agent, or Firm*—Hana Dolezalova

[57] ABSTRACT

Transplants are coated with an insoluble immunological barrier membrane. The membrane can comprise a non-cytotoxic first layer of agarose and cationic amino acid polymer and a non-cytotoxic second layer chemically bonded to said first layer, the second layer comprising an anionic amino acid polymer. The molecular weight of the anionic amino acid polymer is preferably in the range of 2000 to 500,000 daltons, and the thickness if the total membrane coating is within the range of 1 and 100 microns. Alternatively, the membrane can comprise a non-cytotoxic first layer of a cationic amino acid polymer. A non-cytotoxic second layer chemically bonded to the first layer comprises agarose and an anionic amino acid polymer. A non-cytotoxic optional third layer chemically bonded to said second layer comprises a cationic amino acid polymer. The molecular weight of the cationic acid polymer of the third layer is in the range of from 2,000 to 500,000 daltons and the thickness of the total coating is between 1 and 100 microns. The transplants can be allografts of endocrine cells or tissues such a pancreatic islets. The preferred cationic amino acids are L-lysine, poly-L-arginine, and mixtures thereof, and the preferred anionic amino acids are L-aspartic acid, L-glutamic acid, and mixtures thereof. The coatings are formed by applying corresponding successive solutions to the cells or tissue of the transplant and by forming droplets in immiscible oils.

22 Claims, No Drawings

COATED TRANSPLANT AND METHOD FOR MAKING SAME

This is a continuation of application Ser. No. 07/890,896 filed on May 29, 1992, now abandoned.

FIELD OF THE INVENTION

This invention relates to the field of medical transplants of cells and tissues and their manufacture. More particularly, it relates to transplants that have been coated with an immunological barrier comprising agarose to render them suitable for transplantation and processes for their manufacture.

BACKGROUND OF THE INVENTION

Transplants between immunologically incompatible individuals (called xenografts when the donor and recipient or host are of different species or allografts when the donor and recipient are of the same species) normally induce an immune response in the recipient individual. The immune response often leads to rejection or destruction of the transplant or, if the transplant contains immunocompetent cells, to graft-versus-host disease (GVHD).

Various techniques have been used in an attempt to reduce or eliminate the immunogenicity of transplants. For instance, transplants have been manipulated by culturing under conditions that cause selective elimination or deactivation of cells that stimulate the immune response or by treating the transplant with antisera that recognize receptors on such cells as disclosed in *Transplantation Proceedings* (1982) 14(4):714–723. Pancreatic islets have also been placed in semipermeable polymeric containers, called "diffusion pouches" in attempts to make an artificial pancreas as described in *Diabetes* (1977) 26:1136–9 and *Trans. Am. Soc. Artif. Intern. Organs.* (1979) 25:74–76. Biological objects have also been passively trapped in a gel which has no affinity for the living biological object tissue. The gel layer must necessarily be thick in order to completely surround the biological object.

U.S. Pat. No. 4,663,286 (Tsang et al.) discloses a gel system wherein viable cells are encapsulated using an alginate polymer. The gel layer is subsequently cross-linked with a polycationic polymer such as polylysine. A second membrane layer can be formed by contacting the capsules with a second polycationic polymer, such as polyornithine solution, or by exposure to a more highly charged density polymer such as polyvinyl amine. The second layer can, in turn be coated with alginate.

U.S. Pat. Nos. 4,806,355, 4,689,293, and 4,673,566 to Goosen et al., describe the microencapsulation of islets in a hydrogel for subsequent transplantation. The microcapsules are composed of an alginate first layer which is crossed-linked using a polyamino acid such as polylysine. Finally, a second outer, negatively charged gel layer is present and is preferably composed of sodium alginate.

U.S. Pat. Nos. 4,409,331, 4,407,957, 4,391,909 and 4,352,883 to Lim and U.S. Pat. Nos. 4,749,620 and 4,744, 933 to Rha et al., variously describe methods of encapsulating biological material using a membrane formed by the interaction of an anionic polymer, such as alginate, with a cationic polymer such as polylysine.

U.S. Pat. No. 4,803,168 to Jarvis describes a cell-containing capsule composed of a glycopolysaccharide first layer and a polyanionic polymer second (outer) layer.

U.S. Pat. No. 4,778,749 to Vasington et al, is directed to methods for entrapping biological material in an alkali earth metal alginate. No additional ionic layers are present.

U.S. Pat. No. 4,647,539 to Mosbach et al., pertains to the immobilization of biological material by encapsulation in polymer beads. Encapsulation is accomplished by adding the biomaterial to an aqueous polymer solution such as an agar or agarose mixture. The biomaterial/polymer solution is then dispersed in a water-insoluble dispersion medium of oil such as soybean oil, and the agar is allowed to gel.

Nilsson et al., *Nature.* (1983) 302:629–630, describe the encapsulation of animal cells in agarose beads formed by cooling a cell-agarose suspension in oil.

U.S. Pat. No. 4,696,286 to Cochrum which is herein incorporated by reference in its entirety describes the preparation of transplants for transplantation into immunologically incompatible individuals. The transplant is coated with an immunological barrier membrane that conforms to the surface of the transplant. The membrane comprises a non-cytotoxic first layer that is bonded chemically to the surface of the transplant and a second (outer) biologically compatible, water-insoluble semipermeable layer bonded chemically to the first layer.

A difficulty that may occur in the application of the above described method is that the first layer will only bond chemically with cell surface molecules found on living tissue. Therefore, biological objects that have dead tissue clinging to their surface only receive a partial capsule.

SUMMARY OF THE INVENTION

The present invention is based on the discovery of an improved coating for biological material for transplant that insures complete encapsulation of the same. In order to form a capsule that completely covers the biological object, a first layer and an optional second, intermediate layer are formed. These two layers together must be thick enough to allow for formulation of a complete, unbroken outer layer, but thin and permeable enough to allow free diffusion of gases, nutrients, and hormones. The affinity of the first layer for the surface of the biological object allows for the thinness of the layer.

One transplant of this invention suitable for transplantation into an immunologically incompatible individual is coated with an insoluble immunological barrier membrane. The barrier membrane comprises a noncytotoxic first layer of a gellable organic polymer and a cationic polymer. The first layer can comprise polysaccharide, e.g., agarose as the gellable polymer and, as the cationic polymer, cationic amino acid polymer. A non-cytotoxic, water-soluble, semi-permeable second layer is chemically bonded to the first layer. Typically, the second layer comprises an anionic amino acid polymer. The molecular weight of the anionic amino acid polymer is preferably in the range of 2000 to 500,000 daltons. The thickness of the total barrier membrane coating is within the range of 1 and 100 microns. The barrier conforms substantially to the surface of the transplant.

Another transplant of this invention suitable for transplantation into an immunologically incompatible individual is coated with an insoluble immunological barrier membrane that conforms to the surface of the transplant. The membrane comprises a non-cytotoxic first layer comprising a cationic amino acid polymer. A non-cytotoxic second layer chemically bonded to the first layer comprises a polysaccharide such as agarose and an anionic, preferably amino acid polymer. Preferably, a non-cytotoxic third layer which comprises a cationic amino acid polymer is chemically bonded to said second layer. The molecular weight of the cationic acid polymer of the third layer is in the range of from 2,000 to 500,000 daltons and the thickness of the total coating is between 1 and 100 microns.

One process of this invention for coating a transplant to make it suitable for transplantation into an immunologically incompatible host comprises coating the transplant with a first layer of a non-cytotoxic solution comprising gellable polymer, e.g., agarose, and a cationic polymer such as a cationic amino acid polymer. The first layer is overcoated by and chemically bonded to a second layer comprising an anionic amino acid polymer.

Another process of this invention for coating a transplant to make it suitable for transplantation into an immunologically incompatible mammal comprises coating the transplant with a non-cytotoxic first layer containing a cationic amino acid polymer. The first layer is then overcoated by and chemically bonded to a non-cytotoxic second layer that includes a polysaccharide and an anionic amino acid polymer. In this process, the second layer can then be overcoated by and chemically bonded to a non-cytotoxic third layer that includes a cationic amino acid polymer.

In the above coated transplants and processes for their manufacture, the transplants can be allografts of endocrine cells or tissues such a pancreatic islets. The preferred cationic amino acids are L-lysine, L-arginine, and mixtures thereof, and the preferred anionic amino acids are L-aspartic acid, L-glutamic acid, and mixtures thereof.

DETAILED DESCRIPTION OF THE INVENTION

The coated transplants of the present invention solve the problems of coated transplants described previously. It is desirable to completely surround the transplant with an immunological barrier such that the transplant will not be rejected by the host. Previously, pancreatic islets were coated with non-cytotoxic materials that would bind to the surface molecules of the living tissue. See, e.g., U.S. Pat. No. 4,696,286 to Cochrum. Where there was dead tissue clinging to the surface of the islet, the surface would receive only a partial coating. The present invention allows for the complete coating of a transplant even in the presence of dead or dying tissue.

Definitions

The term "individual" includes an animal into which the transplant is placed or a donor animal from which the transplant is removed. Individuals include pets, farm animals, laboratory animals and humans.

"Chemically bonded" or "chemical bond" is used to define, and includes, the association between the two layers in the coated transplants. It is to be interpreted broadly to include association through ionic or electrostatic bonds, van der Waals attraction, and/or hydrogen bonds and the like.

"Insoluble" is used to define the property of a membrane to remain substantially intact and not dissolve in aqueous media under the conditions of use.

Transplant Tissues and Cells

The term "transplant" is intended to denote one or more mammalian cells or a multiplicity of associated mammalian cells that comprise an organ from a donor mammal or donor mammals that is (are) immunologically incompatible (xenogeneic or allogeneic) to the intended individual recipient. Included in the term "transplant" are endocrine [pituitary, thyroid, adrenal, parathyroid, thymus, pancreas (islets of Langerhans)] cells or glands. Also included are renal cortex, vascular endothelial, ovarian cells and other cells and tissues from the heart, liver, lung and kidneys. In fact, any living biological object from a single cell to a cluster of cells with about a 1000 micron diameter, even if the object is contaminated with a moderate amount of living or dead tissue, can be encapsulated according to the present invention.

The present invention is applicable to a variety of transplants and is not intended to be limited to a particular type of cell, or organ, or to a particular animal species. Accordingly, while the invention is generally described and further exemplified below with respect to pancreatic islets, it will be appreciated that these teachings may readily be extended to other transplant tissues of other species, including humans.

Pancreatic tissue may be obtained and cultured using known techniques to render it suitable for coating in accordance with the invention. The tissue is obtained fresh and divided by mincing, teasing, comminution, and/or mild digestion with collagenase to facilitate separation of the islets from contaminating cells and materials. The islets may be isolated from the divided/digested pancreatic tissue by washing, filtering, centrifuging or picking procedures. Preferably, the isolate is cultured in a liquid culture medium under conditions and for a time that causes antigenic components (e.g. passenger leukocytes) in the isolate to be deactivated or eliminated. Such media and conditions are described in *Transplant. Proc.* (1982) 14(4):714–23.

Coating Compositions

Agarose, in its various commercial and experimental forms is the preferred neutral non-cytotoxic polysaccharide, coating polymer because it has proper biological characteristics and gels when cooled through various temperatures in the 5°–35° C. range. Representative agarose preparations are FMC's BIOPRODUCT SEAPREP agarose which gels at 8°–17° C. and FMC's SEA PLAQUE agarose which gels at 18°–29° C. Agarose gels under controllable conditions, has affinity for the surface of the transplant, and is biologically compatible. By biologically compatible is meant that the gel is substantially non-antigenic relative to the immune system of the recipient and does not induce a foreign body (fibrosis) reaction or induce a cellular immune response.

Agarose is non-cytotoxic (that is, it does not substantially affect the viability and/or functionality of the transplant to which the material is applied), is low immunologic-response-inducing, and is capable of existing in a liquid (sol) state at a temperature which is low enough to be nondestructive to the transplant. Agarose is capable of forming a gelled (semi-solid) state at a second nondestructive temperature so that the gel-coated islets can be stored at ambient temperature or below. The polymer should also be permeable to glucose, insulin, and other metabolites and molecules necessary to transplant viability so that the coated islets (or other transplants) can function when injected or transplanted. Other polymers, whether natural or synthetic, which meet the requirements above can be used.

The agarose is employed as an aqueous solution. The concentration is such as to completely coat the transplant but still remain liquid until the coating is formed and is about 0.5 to 8 percent by weight, more preferably about 1 to 4 percent by weight, and most preferably 1 percent by weight. Good results are obtained using agarose at about 0.8 to 1.4 percent by weight.

Non-cytotoxic amino acid polymers which are used in preparing the coatings of this invention include the cationic amino acid polymers of L-lysine, L-arginine and mixtures thereof and the anionic amino acid polymers of L-aspartic acid and L-glutamic acid and mixtures.

Non-cytotoxic Immiscible Oil

As will be described below, a preferred embodiment of the process of this invention uses a non-cytotoxic, pharmaceutically acceptable oil to lower the temperature of the gellable polymer containing coating material and effect its gelation without destroying the transplants. Non-cytotoxic, pharmaceutically acceptable oils suitable for this purpose include mineral oils, vegetable oils, e.g., olive oil, sesame seed oil, and silicone oil and the like. Due to its low surface tension, extreme water repellency, and controllable density, silicone oil is preferred and has given excellent results.

Processes

In the following processes, the transplants can be, e.g., allografts of endocrine cells or tissues such as pancreatic islets.

One transplant of this invention suitable for transplantation into an immunologically incompatible individual is coated with an insoluble immunological barrier membrane that conforms to the surface of the transplant. The membrane comprises a non-cytotoxic first layer comprising gellable polymer and cationic amino acid polymer and a non-cytotoxic second layer chemically bonded to said first layer, the second layer comprising anionic amino acid polymer. The molecular weight of the anionic amino acid polymer is preferably in the range of about 2000 to 500,000 daltons, and the thickness of the total coating is within the range of about 1 and 100 microns.

Such a material can be formed as follows:

One process of this invention for coating a transplant to make it suitable for transplantation into an immunologically incompatible individual comprises coating the transplant, e.g., islets, with a first layer of a non-cytotoxic solution comprising agarose and a cationic amino acid polymer. The islets are suspended in a suitable aqueous cell medium solution such as RPMI 1640 solution at a temperature above the gellable polymer (agarose) gelling temperature and up to about 37° C. and mixed with from about 0.5 to 5 wt. percent gellable polymer (agarose) and from about 0.1 to 1 wt. percent cationic amino acid polymer. This effects coating.

The coated islets are then introduced into the oil at a temperature above the agarose gelling temperature up to about 37° C. to form a dispersion of the agarose coated islet droplets, and the suspension is chilled with continuous stirring to a temperature from 4° up to the gelling temperature of the agarose, usually less than 15° C. The cationic acid polymer such as poly-L-lysine or poly-L-arginine chemically bonds with the surface of the islet.

Alternatively, the coated islets are introduced as single droplets into an oil having a temperature below the polymer (e.g., agarose) gelling temperature, i.e., from between 4° and 15° C.

The coated islets are then dispersed in a neutral, physiological saline solution of from 0.1 to 1 wt. percent anionic amino acid polymer such as poly-L-aspartic acid or poly-L-glutamic acid, the anionic polymer chemically reacting with the cationic acid polymer to form a semipermeable immunological barrier coating.

Another process of this invention comprises coating the transplant with a non-cytotoxic first layer consisting essentially of a cationic amino acid polymer. The islets are dispersed in a suitable aqueous solution such as RPMI 1640 containing from 0.1 to 1 wt. percent of a cationic amino acid polymer such as poly-L-lysine or poly-L-arginine, the cationic amino acid polymer reacting with the islet surface.

The first layer is then coated and chemically bonded to a non-cytotoxic second layer that consists essentially of agarose and an anionic amino acid polymer such as poly-L-aspartic acid or poly-L-glutamic acid. This is accomplished by dispersing the islets with the first coating in a suitable aqueous solution such as RPMI 1640 solution at a temperature above the gelling temperature of agarose up to 37° C., containing from 0.5 to 5 wt. percent agarose and from 0.1 to 1 wt. percent anionic amino acid polymer. The coated islets are then introduced into the oil and gelled as described above, either by forming liquid droplets in the oil followed by chilling the oil to a temperature below the agarose gelling temperature or forming individual droplets in oil prechilled below the agarose gelling temperature. The anionic acid polymer chemically bonds with the cationic acid polymer first coating on the surface of the islet.

Optionally and preferably, the second layer is then coated and chemically bonded to a non-cytotoxic third layer that includes a cationic amino acid polymer such as poly-L-lysine or poly-L-arginine. This is accomplished by dispersing the islets in a neutral, physiological saline solution of from 0.1 to 1 wt. percent cationic amino acid polymer, the cationic polymer chemically reacting with the anionic acid polymer to form a semipermeable immunological barrier coating. The molecular weight of the cationic acid polymer of the third layer is in the range of from 2000 to 500,000 daltons and the thickness of the total coating is between 1 and 100 microns.

The contacting of the polymer solution with the transplant will typically be done with mild agitation (to ensure complete coating) for about 4 to 10 minutes per layer. If desired, the outer layer may be formed as a plurality of coats or the same or different polymer.

This invention is further illustrated by the following specific but non-limiting examples.

EXAMPLE 1

Pancreatic Islet Isolation

Fresh pancreatic tissue from a dog was comminuted and placed in Hank's solution containing collagenase to digest connective tissue. The resulting digest was subjected to Ficoll-Hypaque gradient centrifugation to isolate the islets. The isolated islets were cultured for 7 days at 37° C. in RPMI 1640 medium supplemented with 10% fetal calf serum under a moist 5% $CO_2$ atmosphere.

EXAMPLE 2

Two Layer Islet Coating

Isolated dog islets obtained by the process of Example 1 were suspended in 3 ml RPMI 1640 at a concentration of $10^3$ islets per ml. In order to apply the first layer, the RPMI medium was replaced with 3 ml of an aqueous solution that comprises 1.5 percent by weight poly-L-lysine and 1 percent by weight agarose. The poly-L-lysine/agarose/islet solution was injected into rapidly stirred silicone oil using a syringe with a fine needle (size 20 gauge or smaller), according to a modification of the method of Nilsson wherein animal cells are entrapped in agarose beads formed upon cooling a cell-agarose suspension in oil medium. Nilsson et al., *Nature* 302:629 (1983). The oil was cooled after injection to 10° C. with continuous stirring. The coated islet cells were then washed 3 times with 6 ml of 0.5% physiological saline, pH 7.

The second, outer layer was then applied to the coated islets such that the first and second layers would be chemically bonded, that is there will be one or more covalent, ionic and/or hydrogen bonds between the layers. The coated islets were transferred to 3 ml of a 0.5% physiological saline solution of poly-L-aspartic acid, MW 50,000 daltons, and mixed for approximately 10 minutes. The poly-L-aspartic acid was removed, and the coated islets were washed 3 times with 6 ml physiological saline, pH 7. The coated islets were then ready for transplantation.

EXAMPLE 3

Three Layer Islet Coating

Isolated dog islets obtained by the procedure of Example 1 were suspended in 3 ml RPMI 1640 at a concentration of $10^3$ islets per ml. In order to apply the first layer of coating, the RPMI medium was replaced with 3 ml of an aqueous solution that comprises 1 percent by weight poly-L-lysine, MW 50,000, and mixed for approximately 10 min. The poly-L-lysine solution was then removed and the coated islets were washed 3 times with 6 ml of 0.5% physiological saline, pH 7.

The second, intermediate layer was applied such that the first and second layers would be chemically bonded. The coated islets were placed in an aqueous solution that comprised 1 percent by weight poly-L-aspartic acid and 1 percent by weight agarose. The resultant poly-L-aspartic acid/agarose/islet solution was injected into rapidly stirred silicone oil using a syringe with a fine needle according to a modification of the method of Nilsson wherein animal cells are entrapped in agarose beads formed upon cooling a cell-agarose suspension in oil medium. Nilsson et al., *Nature* 302:629 (1983). The coated islets were then washed 3 times with 6 ml 0.5% physiological saline solution, pH 7.

The third, outer layer was then applied to the coated islets such that the second and third layers were chemically bonded. The coated islets were transferred to 3 ml of a 0.5% physiological saline solution of poly-L-lysine, MW 50,000 daltons, and mixed for approximately 10 minutes. The poly-L-lysine solution was removed, and the coated islets were washed 3 times with 6 ml physiological saline, pH 7. The coated islets were then ready for transplantation.

EXAMPLE 4

Intrahepatic Allographs of Pancreatic Islets

Transplantation, Dog

A pancreatectomized dog was transplanted with 17,000 large coated islets (150 μm diameter, islet equivalent of 60,000 islets) coated by the procedure described in Example 2. A suspension of the islets was injected into the portal (splenic) vein. Surgery was conducted under controlled conditions. The catheter was spliced into the vein and tied. Gravity flow of 150 ml of saline containing the coated islets was very smooth. Recovery of the dog was uneventful.

EXAMPLE 5

Intrahepatic Allographs of Pancreatic Islets

Metabolic Study, Dog

This study was conducted to study the metabolic efficiency of intrahepatic coated islets of Langerhans by assaying insulin in the portal, splenic and hepatic veins after glucose challenge. The transplanted dog of Example 4 was studied to determine if insulin could be detected in the hepatic vein following a dextrose bolus administered via the portal vein 19 months following the transplantation with coated dog islets described in Example 4.

After a midline incision, the abdominal cavity was examined. The liver appeared normal in size and color, and the surface of the liver was smooth in both dogs. The area surrounding the duodenum was examined for any remnants of the dog's pancreas. No pancreatic tissue could be found in the healed surgical site.

The splenic and portal veins were cannulated via tributaries. An additional catheter was placed in the portal vein adjacent to the intestine so that more effective mixing of the dextrose bolus could be accomplished entering the liver. The dextrose was injected through this catheter, and blood samples were taken from the portal catheter located adjacent to the gastroduodenal vein.

Catheterization and sampling of the hepatic veins in the dog are difficult. The majority of the hepatic veins are embedded in the liver parenchyma. They are short vessels, and there are twenty or more hepatic tributaries (up to 3 mm in diameter) which drain into the post cava in various places as it passes through the liver. Two sites were sampled to increase the odds of detecting insulin in this study. The jugular vein was exposed, and a catheter was placed in the left hepatic vein under visual and manual observation. This is the largest hepatic vein and serves the left lateral, left medial, quadrate and a part of the right medial lobe. In order to obtain the maximum concentration of insulin, a tributary draining into the left hepatic vein (abdominal) was sampled under direct visual observation as it emerged from the liver. Direct hepatic blood samples were obtained with a 22 gauge needle and syringe.

Heparinized blood samples were taken at time 0 and a loading dose of heparin was administered. Blood (3 mm) was drawn from each site (i.e., hepatic, splenic and portal veins) for control glucose and insulin determination at each time during the control period (i.e., 0 and 10 minutes).

The dextrose bolus doses (0.33 g/kg) were injected over a 5 min span to prevent portal vein streaming and insure mixing with portal blood.

Blood samples were drawn from each site (i.e., hepatic (jugular and direct), splenic and portal veins) at 2, 4, 6, 10 and 20 min following the dextrose bolus.

The livers were removed and carefully inspected for islets and scarring. Any suspect small areas of the liver which might contain encapsulated islets were removed for plastic histology. The entire liver, intestines and a section of the spleen, muscle and kidney were placed in 10% formalin fixative for histology.

Blood samples were tested blindly for insulin levels in two independent laboratories.

The insulin values indicated that the hepatic vein insulin levels rose 2 min after the dextrose bolus and remained above the splenic and portal levels for 4–10 min. Recirculating insulin could be detected in the splenic and portal vessels following the hepatic (transplanted islet) response. The fact that the portal vein showed no insulin response after the dextrose bolus reaffirms that the entire endocrine pancreas had been removed at the time of the pancreatectomy.

The level of insulin release from the transplanted islets (4–7 μIU/ml) was low when compared with a normal dog (32–49 μIU/ml). This was to be expected since only 60,000 islet equivalents (150 μm) were transplanted per dog as compared with approximately 1,000,000 islets in the normal dog.

These studies support the clinical picture of the dogs of reduced insulin requirement 19 months after islet transplantation.

Thus, new improved coatings for biological materials are disclosed. Although preferred embodiments of the subject invention have been described in some detail, it is understood that variations can be made without departing from the spirit and the scope of the invention as defined by the appended claims.

The invention claimed is:

1. A method for coating a tissue transplant with an immunological barrier protecting the transplant against destruction by the immune system of an immunologically incompatible transplant host recipient, said method comprising steps:

(a) isolating the transplant tissue;
   (b) coating the transplant tissue with a first coating by suspending the transplant in an aqueous solution of a mixture of agarose and a cationic or anionic noncytotoxic amino acid polymer at a temperature which renders the agarose to be in a liquid sol state;
   (c) lowering a temperature of the suspension of step (b) until the agarose changes from the liquid sol to a gel;
   (d) coating the transplant with a second coating by dispersing the suspension of step (c) in a solution of an cationic or anionic amino acid polymer having the charge opposite to the amino acid polymer used in the step (b), and chemical bonding the amino acid of the first coating with the amino acid of the second coating, said chemical bonding formed by one or more covalent, ionic or hydrogen bonds between the first and second layer.

2. The method of claim 1 wherein the first coating contains agarose from about 0.5% to about 8%, by weight, and the cationic or anionic amino acid from about 0.1% to 1%, by weight.

3. The method of claim 2 wherein the first coating contains agarose from about 0.8% to about 1.4%, by weight.

4. The method of claim 3 wherein the temperature of step (b) rendering the agarose to be in a liquid sol state is above the agarose gelling temperature and up to about 37° C.

5. The method of claim 4 wherein the first coating mixture of step (b) is chilled to an agarose gelling temperature from about 5° C. to about 35° C. changing the agarose liquid sol into the agarose gel.

6. The method of claim 6 wherein the mixture of step (b) containing the transplant coated with agarose sol is chilled by introducing said mixture into a noncytotoxic, pharmaceutically acceptable oil at a temperature above the agarose gelling temperature and chilling said mixture with continuous stirring to the gelling temperature of the agarose.

7. The method of claim 6 wherein the dispersion of step (d) contains from about 0.1% to about 1%, by weight, of the amino acid polymer.

8. The method of claim 7 wherein the cationic amino acid is selected from the group consisting of L-lysine, L-arginine and a mixture thereof, and the anionic amino acid is selected from group consisting of L-aspartic acid, L-glutamic acid and a mixture thereof.

9. The method of claim 8 wherein the tissue transplant is an allograft.

10. The method of claim 8 wherein the tissue transplant is an endocrine tissue transplant.

11. The method of claim 8 wherein the tissue transplant is a pancreatic islet, wherein the amino acid polymer present in the aqueous agarose solution used for the first coating is poly-L-lysine and wherein the amino acid polymer used for the second coating is poly-L-aspartic acid.

12. The method of claim 8 wherein the cationic amino acid polymer is poly-L-lysine.

13. The method of claim 8 wherein the anionic amino acid polymer is poly-L-aspartic acid.

14. The method of claim 11 wherein the pancreatic islet transplant is additionally coated with a third layer consisting of the poly-L-lysine.

15. A method for coating a tissue transplant with an immunological barrier protecting the transplant against destruction by the immune system of an immunologically incompatible transplant host recipient, said method comprising steps:

(a) isolating the transplant tissue;
   (b) coating the transplant tissue with a first coating comprising a solution consisting of about 0.1% to about 1%, by weight, of a cationic or anionic acid polymer, said amino acid polymer having a charge opposite to a charge on a transplant surface, reacting with the transplant surface charge and forming a chemical bond;
   (c) dispersing the transplant of the step (b) in a second coating solution comprising a mixture of agarose and a cationic or anionic amino acid polymer having charge opposite to the charge of the amino acid polymer of step (b), at a temperature which renders the agarose to be in a liquid sol state; and
   (d) lowering the temperature of the aqueous solution of step (b) until the agarose changes from the liquid sol to a gel.

16. The method of claim 15 wherein the second coating contains agarose from about 0.5% about 8% by weight and the cationic or anionic amino acid is present in 0.1% to 1% by weight.

17. The method of claim 16 wherein the first coating contains agarose about 0.8% about 1.4%.

18. The method of claim 17 wherein the temperature of step (c) rendering the agarose to be in a liquid sol state is above the agarose gelling temperature and up to about 37° C.

19. The method of claim 18 wherein the second coating mixture of step (c) is chilled to an agarose gelling temperature changing the agarose liquid sol into the agarose gel.

20. The method of claim 19 wherein the tissue transplant is an allograft.

21. The method of claim 19 wherein the tissue transplant is an endocrine tissue transplant.

22. The method of claim 19 wherein the tissue transplant is a pancreatic islet, wherein the amino acid polymer used for the first coating is poly-L-lysine and wherein the amino acid polymer present in the aqueous agarose solution used for the second coating is poly-L-aspartic acid.

* * * * *